United States Patent [19]

Novacek et al.

[11] Patent Number: 5,360,404

[45] Date of Patent: Nov. 1, 1994

[54] NEEDLE GUARD AND NEEDLE ASSEMBLY FOR SYRINGE

[75] Inventors: Laurel A. Novacek; Fraser R. Sharp; Donald A. McLean, all of Vancouver, Canada

[73] Assignee: Inviro Medical Devices Ltd., Bridgetown, Barbados

[21] Appl. No.: 136,201

[22] Filed: Oct. 15, 1993

Related U.S. Application Data

[60] Continuation-in-part of Ser. No. 909,385, Jul. 9, 1992, Pat. No. 5,263,933, which is a continuation-in-part of Ser. No. 800,849, Nov. 29, 1991, Pat. No. 5,205,827, which is a division of Ser. No. 687,108, Apr. 18, 1991, Pat. No. 5,112,318, which is a continuation-in-part of Ser. No. 607,127, Oct. 3, 1990, Pat. No. 5,122,124, which is a continuation-in-part of Ser. No. 410,318, Sep. 21, 1989, Pat. No. 5,030,208, which is a continuation-in-part of Ser. No. 327,344, Mar. 22, 1989, abandoned, which is a continuation-in-part of Ser. No. 285,012, Dec. 14, 1988, abandoned.

[51] Int. Cl.$^5$ ............................................. A61M 5/00
[52] U.S. Cl. .................................... 604/110; 604/240
[58] Field of Search ............... 604/110, 187, 192, 263, 604/240, 241, 242, 243, 272

[56] References Cited

U.S. PATENT DOCUMENTS

| | | | |
|---|---|---|---|
| 4,740,205 | 4/1988 | Seltzer et al. | 604/241 X |
| 4,998,924 | 3/1991 | Ranford | 604/110 X |
| 5,053,018 | 10/1991 | Talon et al. | 604/110 X |
| 5,147,325 | 9/1992 | Mitchell et al. | 604/192 |
| 5,205,833 | 4/1993 | Harsh et al. | 604/240 |
| 5,250,037 | 10/1993 | Bitdinger | 604/242 X |

*Primary Examiner*—John D. Yasko
*Attorney, Agent, or Firm*—Nixon & Vanderhye

[57] ABSTRACT

The syringe includes a plunger and an adapter carrying a needle, the adapter being threaded into the end of the barrel for withdrawal, upon connection with the plunger and together with the needle, into the interior of the barrel. To prevent the adapter from unseating from the barrel end before or during use, the needle guard and hub are connected to enable axial pressure from the needle guard to be transmitted through the hub to the adapter to attach the hub to the adapter. Cooperating surfaces on the needle guard and needle hub are engageable to enable a torque to be applied to the adapter only in a direction opposite to the direction of rotation of the adapter during unseating. To the extent rotation of the needle guard in the opposite direction applies a torque to the adapter, that torque is insufficient to unseat the adapter from the barrel end.

18 Claims, 8 Drawing Sheets

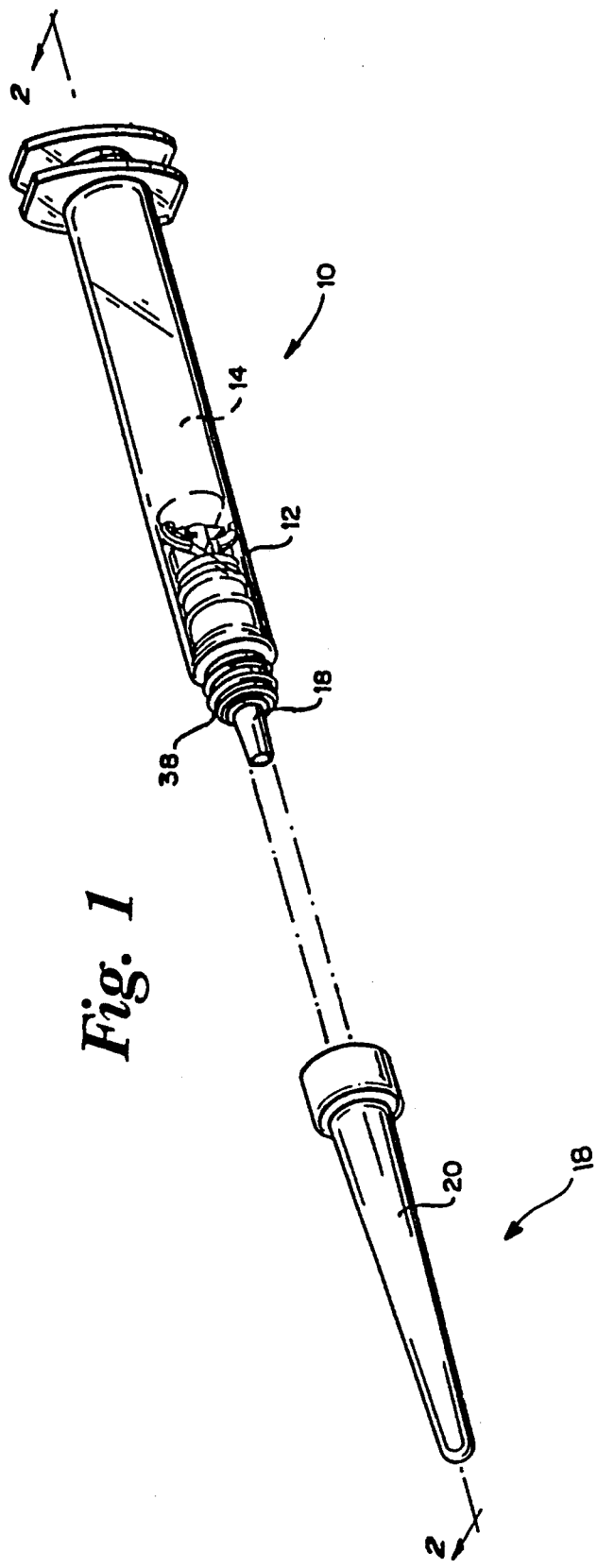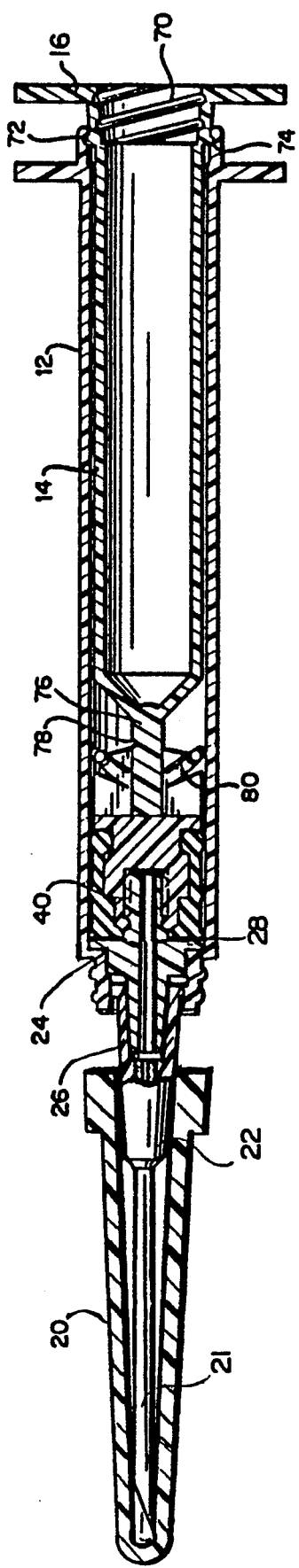

*Fig. 5* *Fig. 6* *Fig. 7*
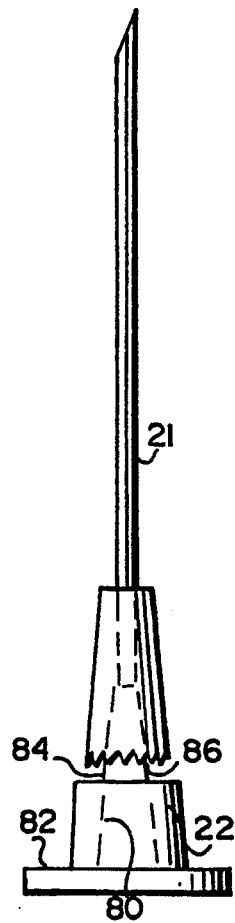
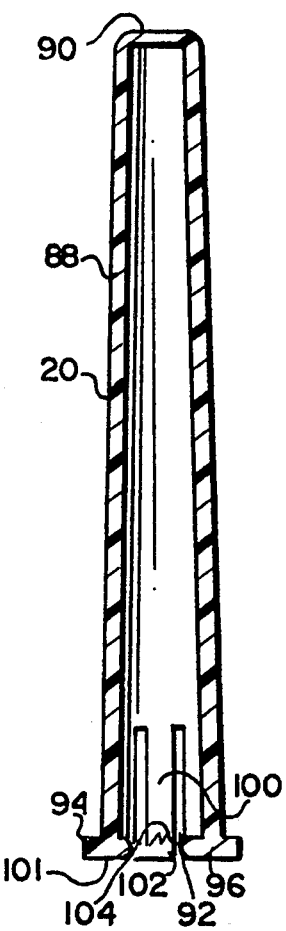
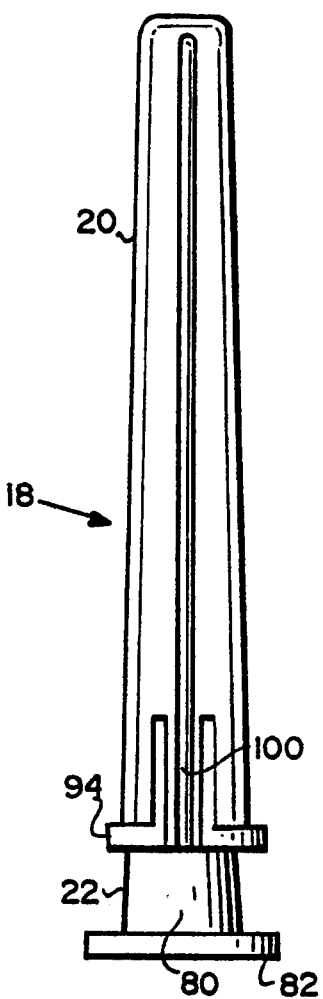
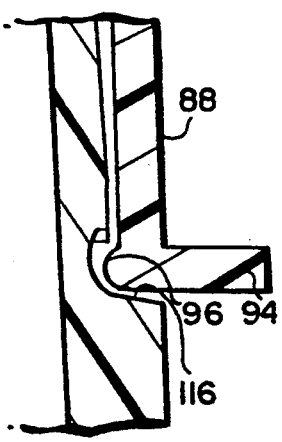
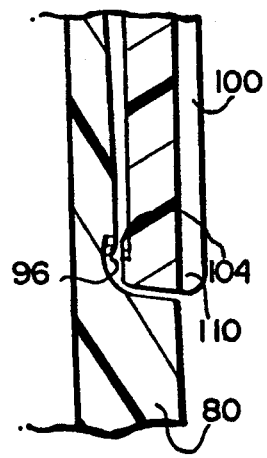
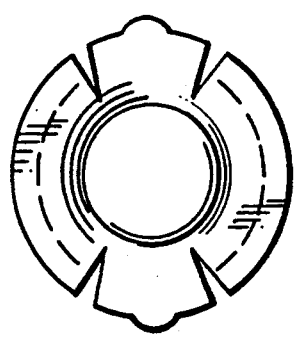
*Fig. 8* *Fig. 9* *Fig. 10*

Fig. 24
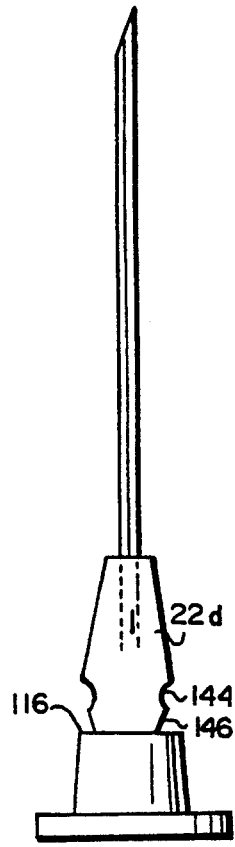
Fig. 25
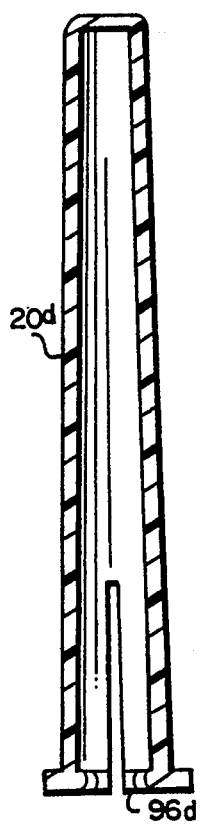
Fig. 26
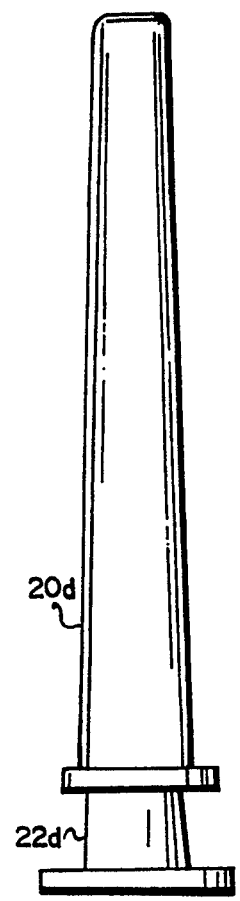
Fig. 28
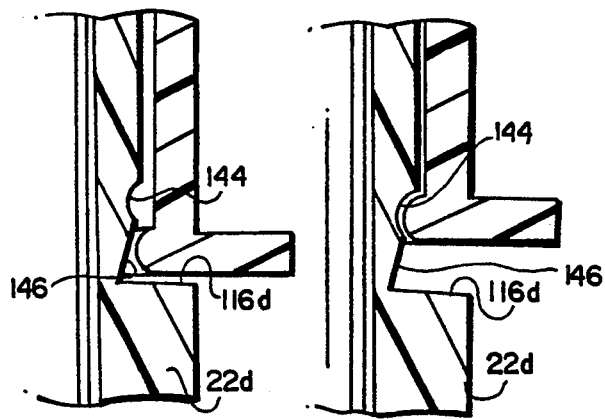
Fig. 30
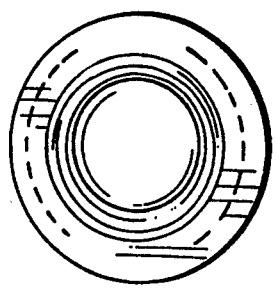
Fig. 27
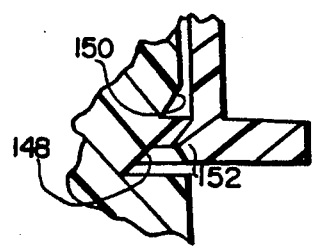
Fig. 29

Fig. 31 Fig. 32 Fig. 33
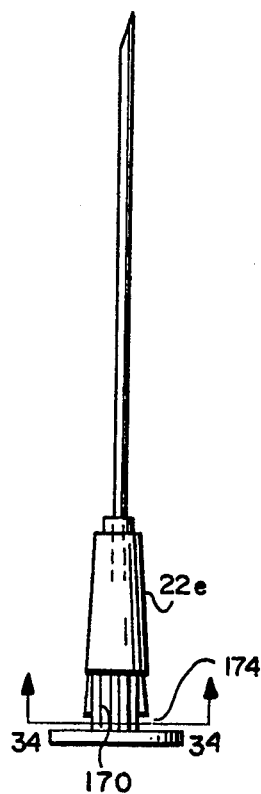
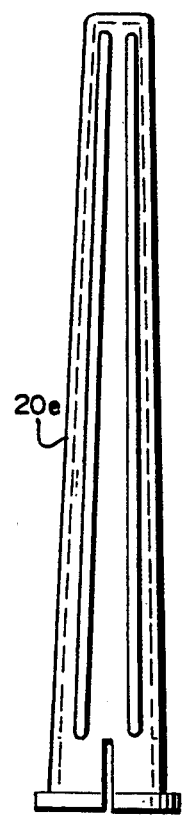
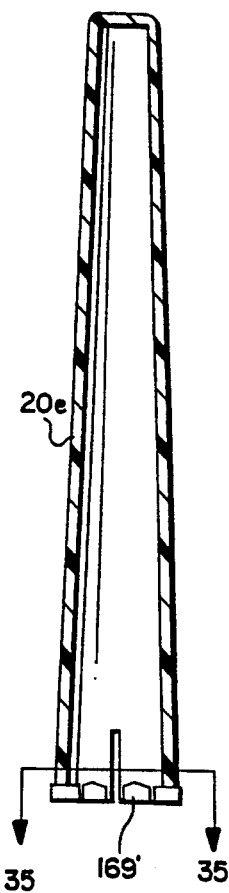
Fig. 34  Fig. 35 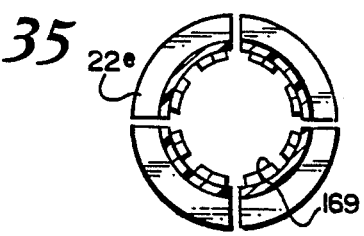
Fig. 36
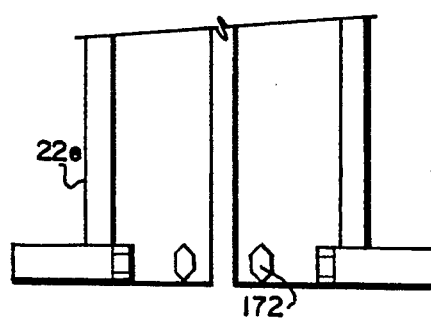

NEEDLE GUARD AND NEEDLE ASSEMBLY FOR SYRINGE

RELATED APPLICATIONS

This application is a continuation-in-part of application Ser. No. 07/909,385, filed Jul. 9, 1992, now U.S. Pat. No. 5,263,933 which, in turn, is a continuation-in-part of application Ser. No. 07/800,849, filed Nov. 29, 1991, now U.S. Pat. No. 5,205,827, issued Apr. 27, 1993, which is a divisional of application Ser. No. 07/687,108, filed Apr. 18, 1991, now U.S. Pat. No. 5,112,318, issued May 12, 1992, which is a continuation-in-part of application Ser. No. 07/607,127, filed Oct. 3, 1990, now U.S. Pat. No. 5,122,124, issued Jun. 16, 1992, which is a continuation-in-part of application Ser. No. 07/410,318, filed Sep. 21, 1989, now U.S. Pat. No. 5,030,208, issued Jun. 9, 1991, which was a continuation-in-part of application Ser. No. 07/327,344, filed Mar. 22, 1989, now abandoned, which was a continuation-in-part of application Ser. No. 07/285,012, filed Dec. 14, 1988, now abandoned, the disclosures of which are incorporated herein by reference.

FIELD OF THE INVENTION

This invention relates to a needle guard and needle assembly for a syringe for medical and industrial application and particularly to a needle guard and needle assembly for use with syringes of the type disclosed in the above-identified patents and patent application wherein, after use, the needle can be withdrawn into the syringe barrel for disposal purposes, thereby eliminating needle stick injuries.

BACKGROUND AND SUMMARY OF THE INVENTION

Needle stick injuries, e.g., among medical personnel such as health care workers, are of growing concern because of disease transmission, particularly the deadly virus known as HIV-1 (AIDS) and Hepatitis B. With presently used syringes having projecting needles, potentially dangerous needle stick injuries are commonplace and most often occur between the time medication is injected into the patient and the time of the disposal of the syringe. Most injuries occur while recapping the needle or when disposing it into a disposal, e.g., "sharps," container. Maintenance personnel who handle disposed materials are also subject to needle stick injuries.

These concerns have been previously addressed as described in our prior U.S. patents and patent application listed above. In these documents, there is disclosed a syringe comprised of a hollow, elongated barrel, an adapter secured to an end of the barrel and releasable therefrom by rotation of the adapter relative to the barrel for withdrawal into the barrel, a plunger movable axially within the hollow barrel, and cooperative engagement structures on the adapter and at the end of the plunger proximate the adapter for engaging and rotating the adapter relative to the barrel to enable the adapter and the needle carried thereby to be withdrawn into the interior of the barrel. Various apparatus are employed to seal the opposite ends of the barrel once the adapter and needle have been withdrawn into the barrel, thereby providing effective protection against potentially dangerous needle stick injuries and contamination by leakage of fluids from the syringe.

It will be appreciated from a review of our prior patents and pending application that the needle can be provided integrally with the adapter or may be provided separately of the syringe. For example, a needle assembly comprised of a needle hub, a needle secured to the hub and a needle guard encasing the needle and at least in part the hub may be provided for attachment by the user of the syringe to the barrel or the adapter. Typically, the needle assembly is secured to the syringe by either a Luer lock or a Luer fit. In both cases, the needle assembly normally includes a needle hub having radially outwardly projecting flanges. In a Luer lock, the needle is secured to the syringe by threading the flanges along a partially female threaded interior portion of the barrel. Alternatively, the needle hub may be frictionally engaged with a projecting tapered fitting on the barrel end. This is typically characterized as a Luer fit and does not have any positive locking action between the needle hub and the tapered projection on the barrel end, other than the frictional engagement. Thus, when a Luer lock is employed, the user of the syringe typically rotates the needle assembly, i.e., the needle guard, needle and needle hub, to positively engage the needle hub with the barrel end. When using a Luer fit, however, only an axial force on the needle assembly toward the syringe is necessary to frictionally engage the needle hub and the tapered projection on the barrel end. In typical syringes, the Luer fit comprises an integral part of the barrel or is at least non-rotationally secured to the barrel.

As a consequence, when attaching needle assemblies to a conventional syringe, frequent users of such syringes typically reflexively rotate the needle guard and needle hub, usually without regard to whether the securement is a Luer lock or a Luer fit (the latter, of course, does not require any rotation for securement of the hub to the barrel end as explained above). Also, when removing the needle assembly from the syringe, for example, when changing needles on the same syringe, the user will typically apply the needle guard and rotate the needle guard and hub relative to the tapered fitting on the barrel to essentially unscrew the hub from the barrel in the case of a Luer lock and to break the static friction between the hub and the fitting in the case of both the Luer lock and Luer fit. Consequently, a rotational force or torque is usually applied to the needle guard to remove a needle from a conventional syringe having a fixed or integral tapered fitting and without consequence to the syringe. However, with the advantageous arrangement of an adapter being removably mounted in the end of the syringe barrel in response to joint rotation of the plunger and adapter when the plunger engages the adapter (as set forth in the above-identified patents and patent application), there is a potential that this reflexive action of the user or any torque applied by the user, intended or otherwise, when applying the needle assembly to or removing it from the syringe could apply sufficient torque to the adapter to unseat the adapter from the syringe from its sealing engagement in the end of the barrel. This inadvertent unthreading or rotation of the adapter relative to the barrel end is highly undesirable, particularly from the standpoint of the close of the seal between the adapter and barrel end which, in turn, would result in fluid leakage. Contamination, in this type of syringe, may also be a problem should the seal be broken by this unthreading action.

According to the present invention, there is provided a needle guard and needle assembly for use with syringes of the type having an adapter removable from the syringe barrel end by rotation of the adapter relative to the barrel end, e.g., to withdraw the needle into the barrel, wherein inadvertent or intentional application of torque to the needle assembly when applying or removing it relative to the syringe will preclude application of torque to the adapter or torque of a magnitude sufficient to unseat the adapter relative to the barrel, and hence prevent the adapter from being unseated from the barrel when applying or removing the needle assembly. To accomplish this, the needle guard and needle hub have cooperable surfaces configured such that a torque applied to the needle guard in one direction is transmitted to the needle hub whereas a torque applied to the needle guard in the opposite direction enables relative rotation of the needle guard and the needle hub without transmission of substantial torque from the needle guard to the needle hub. Thus, if the adapter may be unthreaded from to the barrel end in response to a torque applied to the adapter in one rotational direction, the cooperable surfaces of the needle guard and needle hub are configured such that any torque transmitted from the needle guard to the needle hub in that one direction is insufficient to cause the adapter to unthread from the barrel end. That is, should a torque be applied to the needle guard in the unthreading direction of the adapter, the needle guard will generally freely rotate relative to the hub or will not transmit sufficient torque to the needle hub to cause separation of the adapter from the barrel end. Conversely, a torque applied to the needle guard in the opposite direction may be desirably selectively transmitted to the hub, for example, to break the static friction between the needle hub and the Luer fitting of the adapter so that the needle may be removed from the syringe when changing needles for use with the same syringe. Consequently, the cooperable surfaces of the needle guard and needle hub permit a positive torque to be intentionally applied to the needle hub from the needle guard to break that static friction, but only if the torque is applied in a direction opposite the unthreading direction of the adapter relative to the barrel.

In a preferred embodiment according to the present invention, there is provided apparatus for releasably securing a needle to an end portion of a syringe comprising a needle hub having a needle projecting from one end thereof and a passage through the needle for transmission of a fluid, the needle hub having a surface for engaging the end portion of the syringe and a needle guard including a sleeve closed at one end and open at its opposite end for receiving the needle and a portion of the needle hub within the sleeve, the needle guard and the needle hub having cooperable surfaces, respectively, configured to transmit a torque applied to the needle guard in a first direction to the needle hub and to enable relative rotation of the needle guard and the needle hub without transmission of substantial torque from the needle guard to the needle hub when a torque is applied to the needle guard in a second direction opposite the first direction.

In a further preferred embodiment according to the present invention, there is provided apparatus for releasably securing a needle to a fitting at one end of a syringe comprising a needle hub having a needle projecting from one end thereof and a passage through the needle for transmission of a fluid, the needle hub having a surface for engaging the fitting of the syringe when the hub is secured to the fitting, a needle guard including a sleeve closed at one end and open at its opposite end for receiving the needle and at least a portion of the needle hub within the sleeve, a first pair of cooperable surfaces on the needle hub and the needle guard, respectively, and engageable with one another for enabling a force applied to the needle guard in a first axial direction to be transmitted to the hub for securing the needle hub and the syringe fitting to one another and a second pair of cooperable surfaces on the needle hub and the needle guard, respectively, and engageable with one another for enabling a force applied to the needle guard in a second axial direction opposite the first axial direction to be positively transmitted to the hub for removing the needle hub from the syringe fitting.

Accordingly, it is a primary object of the present invention to provide a novel and improved needle guard and needle assembly for use with a syringe having an adapter removable from the barrel end by rotation of the adapter relative to the barrel wherein torque applied to the needle guard and needle assembly upon application of the needle assembly to and its removal from the syringe will be insufficient to cause the adapter to unseat or unthread from the barrel end.

BRIEF DESCRIPTION OF THE DRAWINGS

FIG. 1 is a perspective view, partially in phantom, of a syringe illustrating a Luer fitting on the adapter of the syringe and a needle guard and needle assembly according to the present invention;

FIG. 2 is a longitudinal cross-sectional view thereof with the needle guard and needle assembly attached to the syringe;

FIG. 5 is an elevational view of a needle and hub sub-assembly according to the present invention;

FIG. 6 is a longitudinal cross-sectional view through a needle guard for use with the sub-assembly of FIG. 5;

FIG. 7 is a side elevational view of a needle assembly of the present invention;

FIGS. 8 and 9 are fragmentary cross-sectional views on an enlarged scale of the juncture between the needle guard and needle hub;

FIG. 10 is a bottom plan view of the needle guard;

FIGS. 24, 25 and 26 are views similar to FIGS. 5, 6 and 7, respectively, illustrating a still further embodiment of the present invention;

FIGS. 27 and 28 are fragmentary enlarged cross-sectional views of the juncture of the needle guard and needle hub of the embodiment of FIGS. 24-26;

FIG. 29 is a view similar to FIG. 27 illustrating an alternate form of the juncture of the needle guard and needle hub;

FIG. 30 is a bottom plan view of the needle guard of FIG. 25;

FIGS. 31, 32 and 33 are views similar to FIGS. 5, 6 and 7, respectively, illustrating a still further embodiment of the present invention;

FIG. 34 is a cross-sectional view thereof taken generally about on line 34—34 in FIG. 31;

FIG. 35 is a bottom plan view of the needle guard of FIG. 33; and

FIG. 36 is an enlarged cross-sectional view of the lower end of an alternative form of the needle guard of FIG. 33.

DETAILED DESCRIPTION OF THE DRAWINGS

Figure 3:
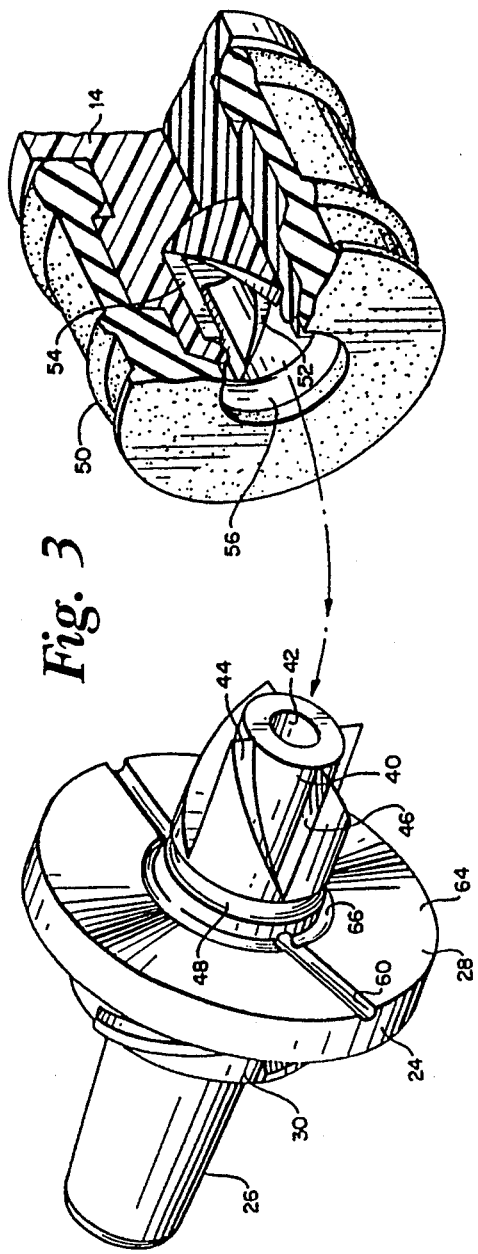
FIG. 3 is a perspective view partially in cross-section of the adapter and the distal end of the plunger, illustrating the mating relationship of these elements.

Referring now to the drawings, particularly to FIGS. 1-4, there is illustrated a syringe, generally designated 10, comprised of a barrel 12 and a plunger 14 having a finger press 16 at the remote end of plunger 14. Also provided is a needle guard and needle assembly, generally designated 18, comprised of a needle guard 20, a needle 21 and a tapered needle hub 22. At the end of the barrel remote from the plunger end thereof, there is provided an adapter 24 which includes a tapered fitting 26, i.e., a Luer fit, for receiving the needle hub 22.

Figure 4:
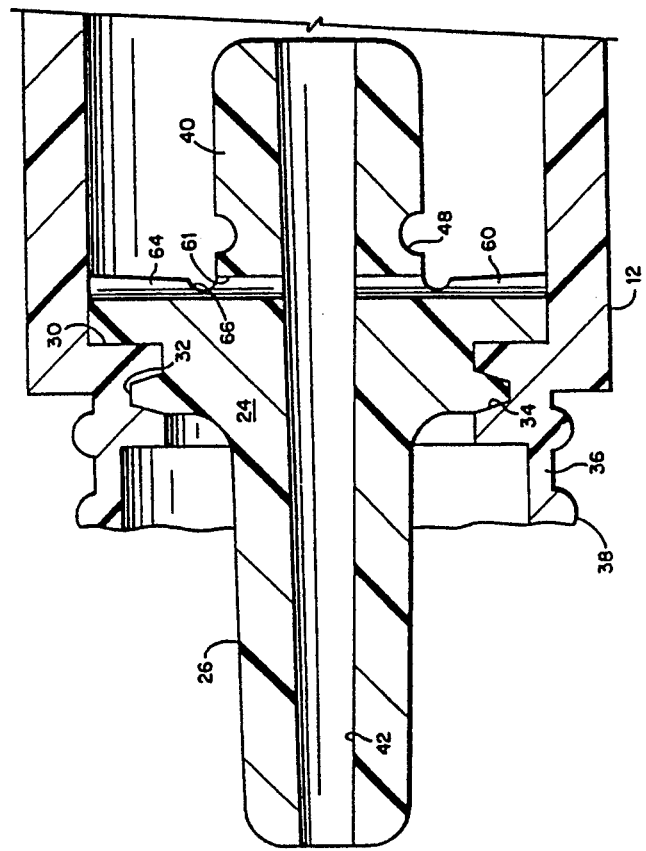
FIG. 4 is an enlarged fragmentary cross-sectional view illustrating the adapter of FIG. 3 disposed on the distal end of the barrel and a portion of the hub of the needle assembly.
Figure 11:
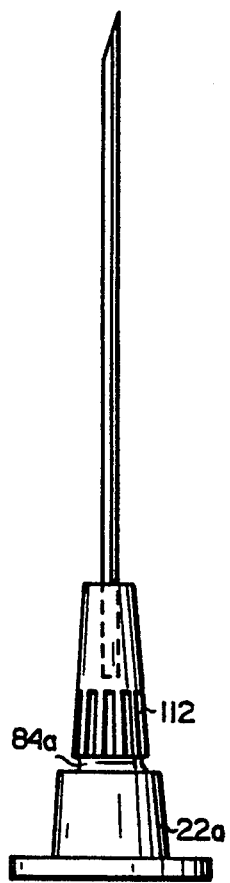
FIGS. 11, 12 and 13 are views similar to FIGS. 5, 6 and 7 illustrating a further form of needle assembly according to the present invention.

Referring particularly to FIGS. 3 and 4, adapter 24 is generally cylindrical, having an annular section 28 for butting against a shoulder 30 at the end of barrel 12. A reduced diameter section has an external thread, for example, a lefthanded thread 32, for engaging with mating threads 34 (FIG. 4) on the reduced diameter end 36 of the barrel. For reasons which will become apparent, the reduced diameter end 36 may also be externally threaded at 38.

Projecting axially from the opposite end of adapter 24 is a protrusion 40 which, when the adapter 24 is secured in the barrel end, projects into the interior chamber of barrel 12. Adapter 24 includes an axially extending tapered channel or passageway 42 for communicating between the interior of the barrel and the needle when the needle assembly is attached. Engagement structure (FIG. 3) extends about the external surface of protrusion 40 for engaging with complementary engagement structure on the plunger whereby the adapter may be removed from the barrel end by rotation thereof and withdrawn, together with the needle, into the interior of the barrel. The engagement structure includes on the external surface of protrusion 40 non-jamming, fast-acting spiral threads or ramps 44, together with axially extending end stops 46. Below ramps 44 is an annular groove 48 which cooperates with the connecting structure on the end of the plunger.

Referring to FIG. 3, the end of the plunger 14 includes a bung 50 formed of resilient material and which surrounds a mating engagement structure on the plunger end for engaging with the structure about protrusion 40. The engagement structure on the plunger includes ramps and end faces 52 and 54, respectively, complementary to the ramps 44 and end faces 46 on protrusion 40. At the distal end of the plunger, there is an inwardly projecting annular rib 56 for engaging in the annular groove 48. Thus, when the plunger is advanced within the barrel to engage protrusion 40, the complementary ramps 44 and 52 engage one another. Due to the slopes of the ramps 44 and 52, the plunger is rotated in one direction relative to the adapter upon axial movement of the plunger toward the adapter to align and engage the end faces 46 and 54 with one another. Further, rotation of the plunger in one direction causes a unidirectional torque to be applied to the adapter, enabling the adapter to be unthreaded from the barrel end. Plunger rotation in the opposite direction causes the end stops 54 and 46 to separate and the plunger to ratchet relative to the adapter.

In operation, when it is desired to withdraw the adapter and needle carried thereby into the barrel, the plunger is advanced axially and guided by the engaging complementary ramps 44 and 52 to engage end stops 46 and 54. Further axial advancement causes full insertion of the plunger into the barrel to engage rib 56 in groove 48. Further rotation of the plunger in one direction unthreads adapter 24 from barrel end threads 34 while maintaining the adapter attached to the plunger end by the engagement of rib 56 and groove 48. Rib 56 may be partially or wholly annular as desired.

To ensure that air from the interior of the barrel may be ejected therefrom prior to use of the syringe, there is provided, with reference to FIG. 3, a pair of vent passages 60 extending radially from and in communication with the central axial passageway 42 through vents 61. These passages preferably extend in grooved portions formed in the face of the flange facing the plunger. Additionally, as illustrated in FIGS. 4 and 5, the face 64 of the adapter facing the plunger is tapered radially inwardly in a direction toward the needle end of the barrel, for example, on the order of 3°. Further, an annular trough or groove 66 is preferably formed in the tapered flange face about the base of protrusion 40. Groove 66 lies in communication with the radial grooves 60 and vents 61 extending into the central passageway 42. One or more additional annular grooves may also be provided, including about the outer margin of the tapered flange base or at intermediate radial positions. By grooving the face of the adapter and tapering that face, grooves 60 and 66 will assume the most superior position within the interior of the barrel when the syringe is oriented vertically with the needle uppermost. Consequently, when the plunger is advanced toward the needle end to vent air from the interior of the barrel, as customary, any air trapped within the annular space between the distal end of the barrel and protrusion 40 will vent through grooves 60, 66 and vents 61 into central passageway 42. Hence, the interior of the barrel may be purged of any air prior to injection. It will be appreciated that there may be only a single vent passage, although preferably at least two such passages diametrically opposed to one another are provided. More than two such passages may also be provided, preferably equally spaced about the axis of the adapter.

Plunger 14 also includes internal threads 70 adjacent finger press 16. An annular ridge 72 on plunger 14 provides sealing engagement with groove 74 formed internally along the distal end of the barrel. Plunger 14 further includes a narrowed portion 76 including a weakened break point 78, as well as a pair of resilient arms or prongs 80.

Once the syringe has been sterilized and assembled, as illustrated in FIG. 2, with the needle guard in place forming a sealing engagement with the threaded barrel, as well as with the plunger in the position shown, forming a sealing engagement between elements 72 and 74, the interior of the structure is thus sealed at both ends, maintaining sterile conditions.

After use, and with the adapter and plunger connected, as illustrated in FIG. 2 and previously described, the plunger may be rotated to disconnect the adapter from the interior threads of the distal end of the barrel. An important feature of this engagement mechanism is that once the adapter has been disconnected at its threaded connection with the barrel, it, along with the needle sub-assembly, i.e., the needle and needle hub, remain attached to the plunger portion through the snap connection formed by the rib 56 and groove 48. Thereafter, the plunger and attached needle sub-assembly may be jointly withdrawn into the barrel.

After the plunger, adapter and needle sub-assembly are withdrawn into the barrel, the ends of the resilient arms 80 register in the annular groove 74 so as to retain the needle sub-assembly and lower portion of the plunger in the barrel. Thereafter, the cylindrical plunger portion may be broken away at the plunger break point 78. After portion 14 has been broken away, it may be attached to the externally threaded distal end of the barrel. Further, description of the operation of the syringe, plunger and adapter may be obtained by reference to the patents and applications referenced earlier.

As noted previously, most disposable syringes can be used with a variety of interchangeable needles with different diameters and lengths connected to the needle barrel by a Luer connector, which may be of two types. One is a simple conical fit or fitting on the syringe which accepts the needle base or hub and frictionally retains the needle on the syringe, known as a Luer tip. To detach the needle, the frictional fit between the needle hub and Luer fit or the adapter is broken and the needle hub is simply pulled off the syringe fitting. The other connector type is known as a Luer lock. The Luer lock has a simple screw thread locking mechanism that permits the hub of the needle to be screwed onto the syringe barrel so that it cannot be pulled off without unscrewing. The needle guard and needle assembly hereof is designed, as will become apparent from the ensuing description, to preclude torque applied to the needle guard, when applying the needle assembly to or removing it from the syringe, to be transmitted to the adapter in a manner which would unseat or unthread the adapter relative to the syringe whether a Luer lock or a Luer fit is used to releasably couple the needle assembly to the syringe.

Referring now to the embodiment hereof illustrated in FIGS. 5–10, the needle 21 of the assembly 18 has an axis and a central passage through needle 21 in communication with a tapered recess 80 within needle hub 22 for transmission of fluid to and from the syringe. Needle hub 22 includes a generally cylindrical base having a radially outwardly directed flange 82 at its proximal end and a groove 84 formed intermediate the proximal and distal ends of the hub 22. The upper portion of the groove 84, as illustrated in FIG. 5, has a plurality of ratchet teeth 86 facing axially toward the syringe when the needle assembly is secured to the syringe.

Referring to FIG. 6, the needle guard 20 includes an elongated sleeve 88 enclosed at its distal end 90 and open at its proximal end 92. The proximal end 92 also has a radially outwardly directed flange 94. A radially inwardly directed rib 96 is formed about the inner surface of the proximal end of the needle guard 20 for cooperation with the groove 84 to releasably secure the needle guard to the needle hub. It will be appreciated that the rib-and-groove arrangement may be reversed, i.e., a radially outwardly directed rib may be formed on the needle hub, while a radially inwardly directed groove may be formed at the proximal end of the needle guard.

To facilitate placing the needle guard onto the needle hub and to apply torque thereto in one direction without substantially transmitting torque to the hub when rotated in the opposite direction, there is provided at least one, and preferably a pair, of diametrically opposed segments 100 cantilevered from the body 88 of the needle guard 20 toward the proximal end 92. The distal end of the segments 100 have a radially inwardly directed rib 102 carrying one or more ratchet teeth 104 disposed in a direction facing the distal end 90 of the needle guard 20. The segments 100 are thus resiliently flexible in radially inward and outward directions.

When the needle guard 20 is disposed over the needle 21 and releasably secured to hub 22, it will be appreciated, as illustrated in FIGS. 8 and 9, that the rib 96 of the needle guard engages in the groove 84. As illustrated in FIG. 8, the ribs 96 are arcuately configured such that an axial force applied to the needle guard away from the hub will enable the sides of the needle guard adjacent the ribs to expand radially outwardly, permitting the needle guard to be removed. The lower side of the groove constitutes a flange or abutment surface 110 which, together with the end face 101 of the ribs 96 and portions of the needle guard, constitute a first set of cooperable surfaces on the needle hub and needle guard engageable with one another, enabling a force applied to the needle guard in an axial direction toward the syringe to be transmitted to the hub for securing the needle hub and syringe fitting to one another. Conversely, the ratchet teeth 86 and 104 on the hub and needle guard, respectively, particularly when segments 100 are pressed inwardly, as well as the rib 96 and opposing ratchet teeth 86 on the needle hub constitute a second set of cooperable surfaces selectively engageable with one another, enabling a force applied to the needle guard in the opposite axial direction, i.e., away from the syringe, to be transmitted to the hub for removing the hub from the syringe fitting.

The segments 100 and ratchet teeth 104 are configured to normally lie radially displaced one from the other, requiring radially inward movement of the segments 100 for the ratchet teeth 104 to engage below the ratchet teeth 86. When moved radially inwardly, and an axial force is applied to the needle guard, tending to separate it from the needle hub, the ratchet teeth engage one another. It will be appreciated that these ratchet teeth are therefore configured to transmit torque applied to the needle guard in one direction to the needle hub and hence permit joint rotation of the needle hub and needle guard in that one direction. Conversely, the ratchet teeth enable relative rotation of the needle guard and needle hub without transmission of substantial torque from the needle guard to the needle hub through the ratcheting teeth 86 and 104 when a torque is applied to the needle guard in the opposite direction.

In use, and assuming the assembly 18 is provided prepackaged and sterilized, the user unpackages the assembly and slips the needle assembly and particularly hub 22 about the Luer fitting of the adapter. By applying an axial force to the needle guard transmitted through the needle hub to the adapter fitting through abutting surfaces 110 and 101, a frictional engagement between the hub and fitting is provided. The needle guard may then be simply displaced in the axially opposite direction to remove it from the hub and to expose the needle. Should the user reflexively rotate the needle guard when applying the assembly 18 to the adapter (without pressing the segments 100 inwardly), it will be appreciated that the needle guard may rotate freely in either direction relative to the adapter on the cooperating surfaces between the proximal end of the needle guard and abutment surface of the hub. Any frictional force or torque thus generated is insufficient to cause rotation of the adapter relative to the barrel.

When it is desired to remove the needle and hub from the adapter, for example, when changing needles on a particular syringe, it is often necessary to rotate the needle hub relative to the Luer fitting to break the static friction between these frictionally engaged elements. To accomplish this, the needle guard is applied to the hub and the segments 100 are pressed inwardly, while at the same time the needle guard is retracted axially and rotated in a direction causing the ratchet teeth to engage one another. Any torque applied to the adapter as a result of the engagement of the ratchet teeth and rotation of the needle guard is in a direction tending to tighten the adapter in the barrel. Any torque applied to the needle guard in the opposite direction causes the teeth to ratchet relative to one another. Consequently, any resulting torque applied to the adapter in the direction tending to unscrew the adapter from the barrel will therefore be insufficient to overcome the frictional resistance of the adapter and barrel connection.

Figure 12:
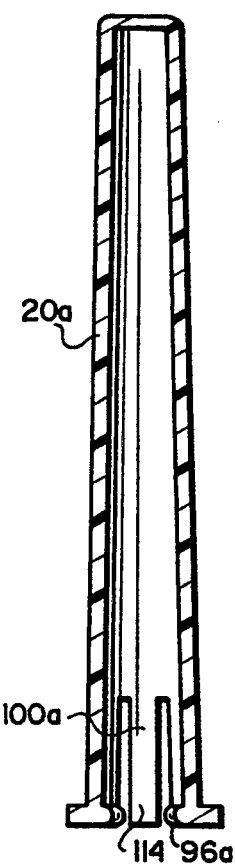
Figure 13:
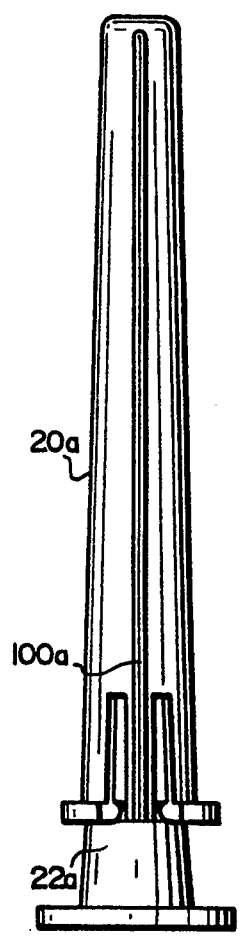
Figure 14:
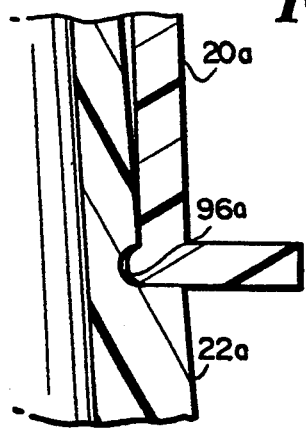
FIG. 14 is an enlarged fragmentary cross-sectional view of the juncture of the needle guard and needle hub of the assembly illustrated in FIGS. 11-13.
Figure 15:
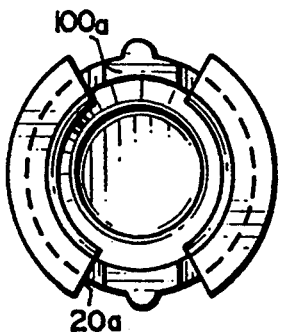
FIG. 15 is a bottom plan view of the needle guard of FIG. 12.
Figure 16:
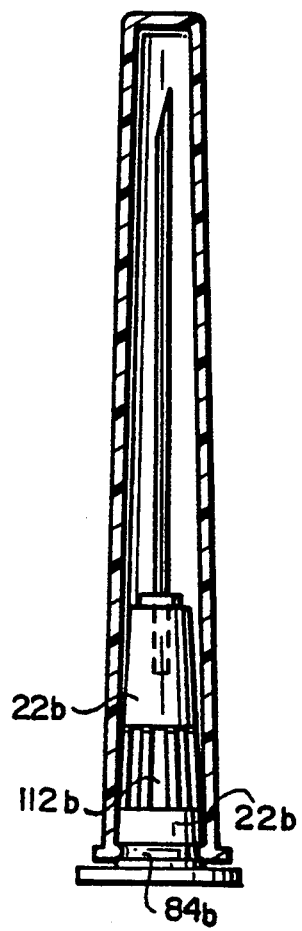
FIG. 16 is a longitudinal cross-sectional view through a needle guard applied to a needle hub according to a further embodiment of the present invention.
Figure 17:
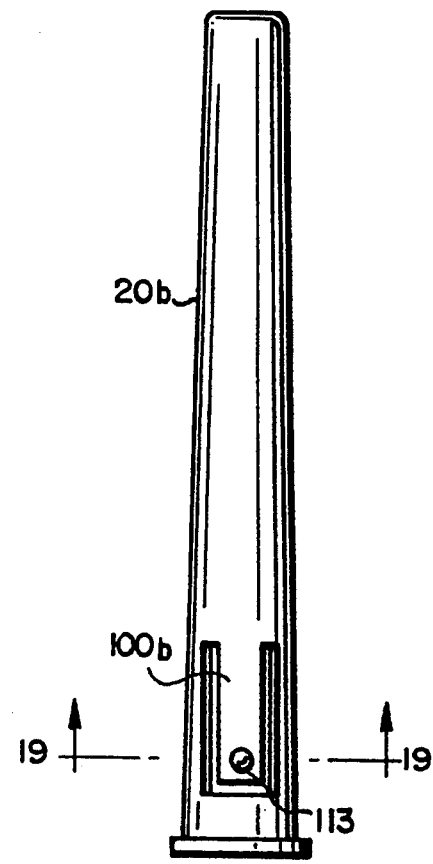
FIG. 17 is an elevational view thereof.
Figure 18:
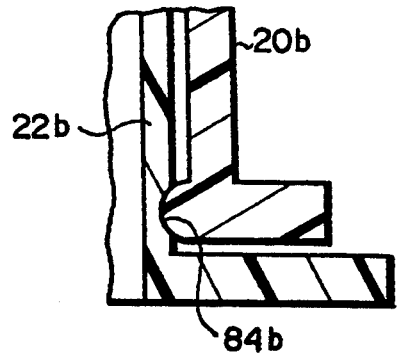
FIG. 18 is an enlarged fragmentary cross-sectional view of the juncture between the needle guard and needle hub of FIG. 16.
Figure 19:
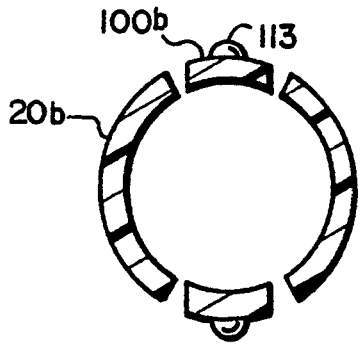
FIG. 19 is a cross-sectional view thereof taken generally about on line 19—19 in FIG. 17.
Figure 20:
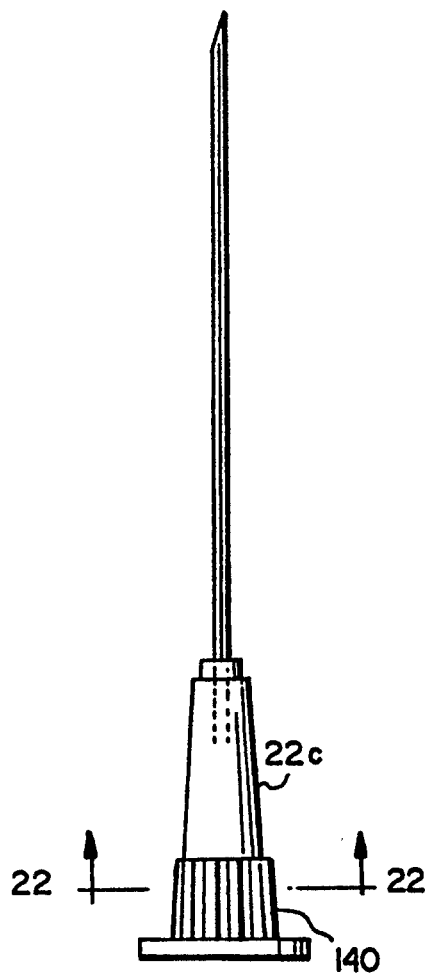
FIGS. 20 and 21 are respective side elevational views of the needle hub and needle guard according to a further embodiment of the present invention.

Referring now to the embodiments hereof illustrated in FIGS. 11-15, wherein like reference numerals are applied to like parts as in the previous embodiment, followed by the suffix "a", the needle hub and needle are essentially the same as illustrated in FIG. 5, with the exception of the omission of the ratchet teeth 86 and the addition of a roughened or serrated surface 112 formed just above the groove 84a. With reference to FIG. 12, the needle guard 20a is similar to the needle guard 20, with the exception of the omission of the ratchet teeth on the segments 100a and the provision of a roughened or serrated edge along the complementary inner face 114 of the segment 100. In this form, as in the previous form, the needle guard is freely rotatable on the needle hub in either direction, the rib-and-groove arrangement releasably securing the needle guard on the needle hub as in the prior embodiment. Thus, when the user wishes to intentionally apply a torque to the hub, for example, to break the static frictional fit between the Luer fit of the adapter and the hub, the segments 100a are pressed radially inwardly to engage the roughened or serrated surface 112. Of course, the needle guard and hub assembly is applied to the syringe and removed therefrom in the manner previously described by making use of the first and second sets of cooperable surfaces, i.e., the ribs 96a and the respective upper and lower portions of the groove 84a.

Referring now to the embodiment hereof illustrated in FIGS. 16-19, like parts are described using like reference numerals as in the previous embodiments, followed by the suffix "b". In this form, the hub 22b has a groove 84b but the groove is located directly adjacent the proximal end of the hub. Spaced toward the distal end of the needle hub from the groove 84b is a roughened or serrated surface 112b. Instead of segments being cantilevered and terminating at the proximal end of the needle guard, the segments 100b terminate spaced from the proximal end of the needle guard. The inside surfaces of the segments 100b have similarly roughened or serrated surfaces for engagement with surface 112b on hub 22b. A protrusion or knob 113 is provided along the external surface of segment 100b to provide the user with a "feel" for the segments 100b. The embodiment of these drawing FIGS. 16-19 is used similarly as previously described with respect to the embodiment of FIGS. 11-15. In this form, however, as well as in any one or more of the other forms, the needle guard can be slit lengthwise, preferably at diametrically opposite locations, to permit the individual opposed portions of the needle guard to flex radially inwardly and outwardly to facilitate attachment and removal of the needle guard relative to the needle hub.

Figure 21:
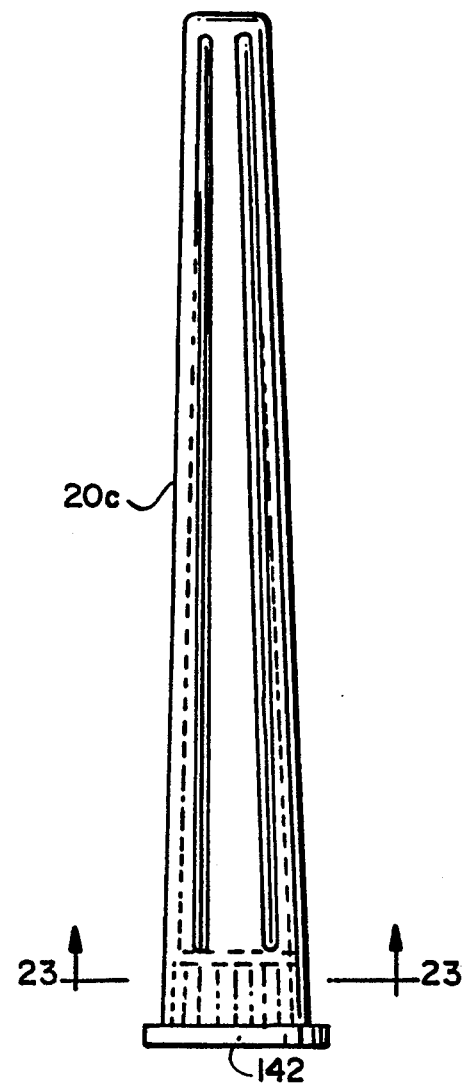
Figure 22:
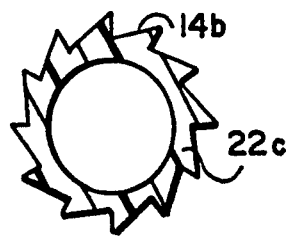
FIGS. 22 and 23 are cross-sectional views thereof taken generally about on lines 22—22 and 23—23 in FIGS. 20 and 21, respectively.
Figure 23:
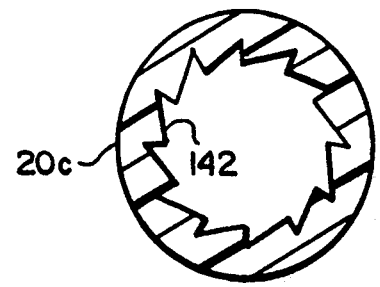

Referring now to the embodiment hereof illustrated in FIGS. 20-23, like parts are described using like reference numerals as in the previous embodiments, followed by the suffix "c." In this form, ratchet-like teeth 140 are formed adjacent the base of hub 22c. The teeth 140 are tapered toward the needle end of the hub. In FIG. 21, the needle guard 20c has complementary-shaped tapered ratchet teeth 142 formed along the inside surface of the guard 20c adjacent its proximal end. Preferably, the needle guard 20c is slotted in the axial direction at diametrically opposed positions such that the opposite halves can be displaced radially inwardly and outwardly. With this arrangement, when it is desired to remove the needle from the Luer fit, the needle guard is rotated in a direction such that the ratchet teeth 140 and 142 engage one another to break the static friction between the needle hub and Luer fit. Rotation of the needle guard in the opposite direction would cause the teeth 140 and 142 to ratchet relative to one another, without transmission of substantial torque to the Luer fit. The direction of engagement of the teeth and the ratcheting action is arranged such that the rotary direction to engage the teeth corresponds to the rotary direction which would tighten the adapter in the end of the barrel. Conversely, the rotary direction of the needle guard relative to the needle hub causing ratcheting of the teeth 140 and 142 corresponds to the rotary direction in which the adapter would be unthreaded from the barrel end. However, the ratcheting action applies insufficient torque to the adapter to permit the adapter to unseat or unthread relative to the barrel end.

Referring now to the embodiment hereof illustrated in FIGS. 24-30, like parts are described using like reference numerals as in the previous embodiment, followed by the suffix "d." In this form, the hub 22d includes a groove 144 and a second groove 146 formed by an annular linear surface. Hub 22d also includes a cooperating abutment surface 116d against which the needle guard 20d abuts to apply axial pressure to the needle hub when applying the needle assembly to the syringe.

The needle guard 20d may be slit longitudinally as illustrated in FIG. 25 such that opposite halves may be displaced radially inwardly or outwardly.

When applying the needle assembly to the syringe, the needle guard lies in its axially retracted position, i.e., the ribs 96d along the inner surface of needle guard 20d adjacent its proximal end engage along the linear surface 146 of the hub as illustrated in FIG. 27. Thus, the cooperating surfaces 116d and the end face of the needle guard enable the needle assembly to be frictionally fit on the Luer fit of the adapter. The needle guard is also freely rotational in opposite directions relative to the hub 22d such that torque applied to the needle guard is not transmitted to the adapter or insufficiently transmitted thereto to cause the adapter to unscrew from the barrel end. When it is desired to remove the needle with the needle guard in its fully home position with ribs 96d engaged in groove 146, an axial withdrawing force is applied and the ribs 96d are thus located in the groove 144 as illustrated in FIG. 28. The surfaces of the groove 144 and rib 96d may be roughened or serrated to enable transmission of torque from the needle guard to the hub. By applying an axial force in a direction away from the syringe, together with an applied torque, by squeezing the sides of the needle guard, the static friction between the hub and the Luer fit is broken. This torque can only be applied to the needle guard upon application of an axial force in a direction away from the syringe to engage 96d and 144 such that any torque applied to the adapter would be insufficient to unseat or unscrew the adapter from the barrel end. In an alternative configuration of this embodiment illustrated in FIG. 29, both of the grooves in the hub 22d may be in the form of tapered grooves 148 and 150, respectively, it being noted that the radially innermost portions of groove 148 have a smaller diameter than corresponding portions in groove 150. Thus, the needle guard is freely rotatable when its complementary-shaped rib 152 extends in groove 148. The lower portion of rib 152 may be rounded or tapered along its underside to ensure that it will slip past groove 148 when the needle guard is applied. When rib 152 bears in groove 150 and the needle guard is axially displaced away from the syringe, torque may be applied to the hub.

Referring to FIGS. 31-36, wherein like reference numerals are applied to like parts as in the prior embodiments, followed by the suffix "e," the base portion of the hub 22e has a series of circumferentially spaced ridges or ribs 168 parallelling the axis of the hub and needle. The axially inner ends of the ridges terminate short of the flange of the hub to permit inwardly directed ribs 169 on the needle guard 20e to freely rotate with the needle guard when applied to the hub. The ribs in this embodiment comprise a series of radially inward, circumferentially spaced, projections having V-shaped or tapered upper surfaces. Thus, when the needle guard is applied to the needle hub, the needle guard is free to rotate in either direction without applying torque to the needle hub. By axially displacing the needle guard from the syringe, the projections are guided between the ribs on the needle hub by the tapered upper ends. When the projections 169 lie between the ribs 170, rotary force applied to the needle guard is transmitted to the hub to break the static friction. With the continuing withdrawal of the needle guard during the application of this torque, insufficient torque is provided the adapter to unseat it from the barrel end.

In the embodiment illustrated in FIG. 36, the lower ends of the projections 172 are also tapered or V-shaped. This facilitates application of the needle guard to the needle hub such that the projections 172 align between the ribs 168 for passage into the lower groove 174 below the ribs and adjacent the hub flange.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. Apparatus for releasably securing a needle to an end portion of a syringe comprising:
a needle hub having a needle projecting from one end thereof and a passage through said needle for transmission of a fluid, said needle hub having a surface for engaging the end portion of the syringe; and
a needle guard including a sleeve closed at one end and open at its opposite end for receiving said needle and a portion of said needle hub within said sleeve;
said needle guard and said needle hub having cooperable surfaces, respectively, configured to transmit a torque applied to said needle guard in a first direction to said needle hub and to enable relative rotation of said needle guard and said needle hub without transmission of substantial torque from said needle guard to said needle hub when a torque is applied to said needle guard in a second direction opposite said first direction.

2. Apparatus according to claim 1 wherein said needle has an elongated axis, said needle guard being substantially freely rotatable relative to said needle hub in at least one rotational direction about an axis parallel to or coincident with the axis of said needle.

3. Apparatus according to claim 1 wherein said cooperable surfaces comprise ratchet teeth on said needle guard and said needle hub engageable with one another in response to the torque applied to said needle guard in said first direction and relatively movable past one another in response to the torque applied to said needle guard in said second direction.

4. Apparatus according to claim 1 wherein said cooperable surfaces include a surface carried by said needle guard movable between a first position spaced from said hub and a second position engageable with another of said cooperable surfaces carried by said hub.

5. Apparatus according to claim 1 wherein said needle has an axis, said needle guard being substantially freely rotatable relative to said needle hub in said first and second directions about an axis parallel to or coincident with said needle axis, a member carried by said needle guard and movable between a first position spaced from said hub and a second position engageable with said hub, said member carrying one of said cooperable surfaces, said member in said second position having said one of said cooperable surfaces in engagement with another of said cooperable surfaces enabling the torque applied to said needle guard in said first direction to be transmitted through said cooperable surfaces to said needle hub.

6. Apparatus according to claim 1 including releasable retaining structure carried by said needle hub and said needle guard for releasably securing said needle hub and said needle guard to one another.

7. Apparatus according to claim 6 wherein said releasable retaining structure includes a rib carried by one of said needle guard and said needle hub and a groove carried by another of said needle guard and said needle hub, such that said rib and said groove are engageable with one another to secure said needle guard and said needle hub to one another.

8. Apparatus according to claim 7 wherein said needle has an axis, said needle guard having at least one slot extending along said sleeve generally parallel to said axis and enabling portions of said sleeve carrying said rib or groove to expand and retract upon application of said needle guard to and removal thereof from said needle hub.

9. Apparatus according to claim 1 wherein said cooperable surfaces comprise ratchet teeth on said needle guard and said needle hub engageable with one another in response to the torque applied to said needle guard in said first direction and movable past one another in response to torque applied to said needle guard in said second direction, said needle guard including a member carried by said needle guard and carrying said ratchet teeth, said member being movable between a first position spaced from the ratchet teeth carried by said needle hub and a second position engageable with the ratchet teeth carried by said hub.

10. Apparatus according to claim 9 wherein said needle has an elongated axis, said ratchet teeth on said needle hub and said needle guard lying in axial opposition to one another.

11. Apparatus according to claim 1 wherein said needle guard and said needle hub have a first pair of cooperable surfaces respectively engageable with one another for enabling a force applied to said needle guard in a first axial direction to be transmitted to said needle hub for securing said needle hub and the end portion of the syringe to one another, and a second pair of cooperable surfaces on said needle hub and said needle guard, respectively, and engageable with one another for enabling a force applied to said needle guard in a second axial direction opposite said first axial direction to be transmitted to said hub for removing said needle hub from the end portion of the syringe.

12. Apparatus according to claim 1 in combination with a syringe having an axially elongated barrel for containing a fluid, an adapter removably mounted at one end of the barrel in response to rotation thereof in said second direction and having a fitting for receiving said needle hub, a plunger axially movable in said barrel and engagement structure cooperable between said plunger and said adapter for removing said adapter from said one barrel end in response to joint rotation of said plunger and said adapter in said second direction upon engagement thereof with one another whereby torque applied to said needle guard is prevented from rotating said adapter relative to said barrel in a direction tending to remove the adapter from the one barrel end.

13. Apparatus for releasably securing a needle to a fitting at one end of a syringe comprising:

a needle hub having a needle projecting from one end thereof and a passage through said needle for transmission of a fluid, said needle hub having a surface for engaging the fitting of the syringe when the hub is secured to the fitting;

a needle guard including a sleeve closed at one end and open at its opposite end for receiving said needle and at least a portion of said needle hub within said sleeve;

a first pair of cooperable surfaces on said needle hub and said needle guard, respectively, and engageable with one another for enabling a force applied to said needle guard in a first axial direction to be transmitted to said hub for securing said needle hub and the syringe fitting to one another; and a second pair of cooperable surfaces on said needle hub and said needle guard, respectively, and engageable with one another for enabling a force applied to said needle guard in a second axial direction opposite said first axial direction to be positively transmitted to said hub for removing said needle hub from the syringe fitting.

14. Apparatus according to claim 13 wherein said needle guard is substantially freely rotatable relative to said needle hub about an axis parallel to said first and second directions.

15. Apparatus according to claim 13 wherein said second pair of cooperable surfaces are engageable with one another and said first pair of cooperable surfaces are spaced from one another in response to application of said force in said second direction.

16. Apparatus according to claim 13 wherein said second pair of surfaces, when engaged, are configured to transmit a torque applied to said needle guard in a first direction to said needle hub and to slip relative to one another when a torque is applied to said needle guard in a second direction opposite said first direction so that said needle guard may rotate relative to said hub without transmission of substantial torque from said needle guard to said needle hub in said second direction.

17. Apparatus according to claim 13 wherein said needle guard is substantially freely rotatable relative to said needle hub about an axis parallel to said first and second directions, a member carried by said needle guard and movable between a first position spaced from said hub and a second position engageable with said hub, said member carrying one of said second pair of surfaces, said member in said second position having said one of said second pair of surfaces in engagement with another of said second pair of surfaces enabling a torque applied to said needle guard to be transmitted through said second pair of surfaces to said needle hub.

18. Apparatus according to claim 17 wherein said second pair of surfaces, when engaged, are configured to transmit a torque applied to said needle guard in a first direction to be transmitted to said needle hub and to slip relative to one another when a torque is applied to said needle guard in a second direction opposite said first direction to minimize any torque in said second direction by said needle guard to said needle hub.

* * * * *